United States Patent [19]

Greenberg et al.

[11] Patent Number: 5,170,362
[45] Date of Patent: Dec. 8, 1992

[54] REDUNDANT SYSTEM FOR INTERACTIVELY EVALUATING THE CAPABILITIES OF MULTIPLE TEST SUBJECTS TO PERFORM A TASK UTILIZING A COMPUTERIZED TEST SYSTEM

[75] Inventors: Howard L. Greenberg, Huntington Beach; Ensor Rodriguez, San Marino, both of Calif.

[73] Assignee: Atlantic Richfield Company, Los Angeles, Calif.

[21] Appl. No.: 641,218

[22] Filed: Jan. 15, 1991

[51] Int. Cl.$^5$ ............ G06F 15/20; G06F 15/42
[52] U.S. Cl. ................... 364/550; 128/745; 364/400; 434/323
[58] Field of Search .......... 364/400, 401, 410, 419, 364/514, 550; 340/825.06; 434/29, 62, 99, 323, 333, 334, 336, 350, 353

[56] References Cited

U.S. PATENT DOCUMENTS

| | | | |
|---|---|---|---|
| 4,012,848 | 3/1977 | Diament et al. | 364/419 X |
| 4,712,180 | 12/1987 | Fujiyama et al. | 364/419 |
| 4,764,120 | 8/1988 | Griffin et al. | 364/419 X |
| 4,894,777 | 1/1990 | Negishi et al. | 364/419 |
| 4,949,248 | 8/1990 | Caro | 364/400 X |
| 4,958,284 | 9/1990 | Bishop et al. | 364/401 X |
| 4,992,940 | 2/1991 | Dworkin | 364/401 |
| 5,058,008 | 10/1991 | Schumacher | 364/401 |
| 5,059,127 | 10/1991 | Lewis et al. | 364/419 X |

Primary Examiner—Kevin J. Teska
Attorney, Agent, or Firm—Robbins, Dalgarn, Berliner & Carson

[57] ABSTRACT

A redundant interactive subject evaluation system composed of multiple, distinct test sites containing multiple test stations, nodes which interconnect several test sites and a single integrating evaluating hub into which flows all site and node data. The system is operable to receive dial-in telecommunications data from any remote test site location including transportation vehicles in transit by air, water, or land. System reliability is high with continued node and test site activity even during overall system outages. The performance evaluation test runs on the test stations at the individual sites interactively evaluating the performance capabilities of multiple subjects by comparing the test subjects' hub data stored as historical performance characteristics with their new test results secured at the test stations. Trained, evaluating personnel not located at the test sites such as Medical Review Officers (MRO's) are located at the nodes and hub to analyze, evaluate and interpret data received from the test subject's results at the remote sites. One embodiment of the system is described in detail.

14 Claims, 4 Drawing Sheets

REDUNDANT SYSTEM FOR INTERACTIVELY EVALUATING THE CAPABILITIES OF MULTIPLE TEST SUBJECTS TO PERFORM A TASK UTILIZING A COMPUTERIZED TEST SYSTEM

FIELD OF THE INVENTION

The present invention relates generally to a redundant interactive testing system for individuals; and more particularly to the testing of multiple subjects at remote sites by comparison of their immediate test results to a centrally stored, base line generated by the results from previously taken tests thereby ascertaining whether or not the subject is capable of performing a particular task.

BACKGROUND OF THE INVENTION

The effects of alcohol, drugs (both ethical and illegal), fatigue, stress, emotional disturbance and the like have long been known to degrade both the physical and mental performance of human beings.

Such degradation of performance may, in certain critical tasks, result in substantial loss of life or property. For example, impaired performance of a ship captain may result in improper response to unusual weather conditions leading to the sinking of the ship, total destruction of the vessel, its cargo and possible long term environmental catastrophe.

Impaired functional capabilities of operators of other types of vehicles can also lead to similar results, for example, pilots, bus or truck drivers carrying cargo or passengers. Individuals operating complex or sensitive equipment may likewise make decisions or take actions which could result in the occurrence of loss of property and human life.

Employers have a two-fold problem. First, they must not hire individuals who place themselves and others at risk due to the effects of substance abuse on their work performance. Second, the employer has a moral and legal responsibility to their shareholders and society at large to monitor their current employees for decreased performance.

Many attempts have been directed to intrusive and non-intrusive testing of individuals to ascertain whether or not their bodies contain performance degrading substances. The testing of individuals in this manner has raised many legal, ethical and moral issues and in many instances is inadequate.

Particularly, such testing will not disclose performance degradation due to emotional disturbance, stress, debilitation as a result of age or disease or the like.

Accuracy and legal and employee morale problems with drug testing have discouraged many employers from implementing widespread drug testing programs. Existing drug tests detect not the drug itself, but the by-products called metabolites that are left behind after the drug has been metabolized by the body. Since these by-products linger in the body for weeks, it is entirely possible and even likely that a subject who fails a drug test is totally sober and fit for work.

Most current non-intrusive drug tests require taking a sample of the employee's urine, a bodily function that most people consider intensely private. The problem is compounded by the growing tendency of employers to observe the employee in the act of urination to prevent cheating. It would be most useful to evaluate an employee's performance capabilities without embarrassing invasive testing methods.

NASA developed the first non-intrusive testing system called "Critical Tracking Task" (CTT), in the 1960's for astronauts and test pilots. Because non-intrusive performance testing detects impairment from any source including illness, emotional problems, or staying up all night with a sick child, it is vastly superior to drug testing for detecting those who pose a safety risk in critical fields such as transportation.

Moreover, because CTT looks only at the test subject's fitness for duty and not off-duty conduct, and does not involve any intrusive or embarrassing procedures, CTT eliminates the employee morale backlash and lawsuits caused by random drug tests.

Other attempts have been made to test individuals on a non-intrusive basis or without the necessity of testing breath or urine samples. For example, the U.S. Pat. No. 3,901,215 to Erwin Roy John entitled, "Method of Testing the Senses and Cognition of Subjects," discloses a system which produces an electroencephalograph on a subject in response to predetermined stimuli where response is compared to the subject's evoked response at a base line condition to ascertain differences between the two. Any differences between past and present performance are automatically statistically analyzed by a computer to ascertain the significance thereof. Obviously, such apparatus as described by the John patent requires complex sensors and highly trained testing personnel to provide the stimuli to the subject and record the results emanating from the subject's brain, establishing both the base line and the subject's response to the stimuli.

Other conventional performance testing such as apparatus (both automotive vehicle and aircraft) have been developed to test the capability of an operator or subject to perform pre-selected critical tasks in advance of assuming work positions to carry out such tasks. Simulators are typically programed so that the operator or subject performs tasks (driving/flying) which are normally performed in the day-to-day work of that individual. The generated test results are compared against proper objective responses anticipated of subjects performing in similar circumstances.

Although such simulators are generally effective, they do not compare the subject's present capabilities of performance against that same subject's previously established performance response capabilities. Furthermore, simulators, even the most simple, are relatively expensive and the use of them exclusively for testing instead of training requires a substantial amount of time.

Subjects engaged in high stress, repetitive work, such as airline pilots making repeated take-offs and landings, chemical plant operators processing toxic materials, nuclear power plant technicians maintaining and cleaning power plant facilities, and surgeons performing countless operations in a limited time period would benefit from immediate feedback on their current performance level. Their employers would not only increase production efficiency but would also increase the level of on the job safety for their employees and the public at large.

SUMMARY OF THE INVENTION

The present invention provides a system for interactively evaluating the capabilities of a subject for performing a task at a remote test site where the subject uses a computer to take a performance evaluation test.

The subject's current level of performance produces data from the current test which is sent to an offtesting node site for comparison with the subject's previous level of performance on the same tests. Besides data storage capability the node site may have an on site human evaluator to review, analyze and compare the subject's current level of performance with the subject's previous level of performance.

A hub site connected to the node site serves as the central data storage and evaluation facility for the subject's current level of performance. In the event of an overall system outage the node site redundantly replaces the hub site.

This invention produces a performance evaluation system that is implemented in a controlled consistent manner using existing technology having reliable characteristics. More particularly, the invention provides a redundant system for interactively evaluating the performance capabilities of known subjects by measuring their response to a series of randomly generated tests and then comparing the test results using an algorithm which statistically passes individuals relative to their predetermined performance level. Multiple failures of the randomly generated tests raise the presumption that the subject's performance is impaired at the time the test is performed. Trained evaluators make the final determination of the subject's fitness to work.

BRIEF DESCRIPTION OF THE DRAWINGS

A complete understanding of the present invention and the above advantages may be gained from a consideration of the following description of the preferred embodiments taken in conjunction with the accompanying drawings in which.

DETAILED DESCRIPTION

The invention, a redundant system for evaluating the performance capabilities of subjects by interactive testing, compares the subjects' current performance test results with stored data representing the subjects' previous performance results. The subjects interactively respond to a multi-function performance test presented to them on a personal computer. The subject's test results are sent through telecommunications lines to offsite data storage and evaluation facilities. A determination of the subject's performance capability is made by comparison of the current test results to that subject's stored historical test results. A decision is made at the offtest site based on this comparison as to whether that subject can perform his assigned duties effectively.

Figure 1:
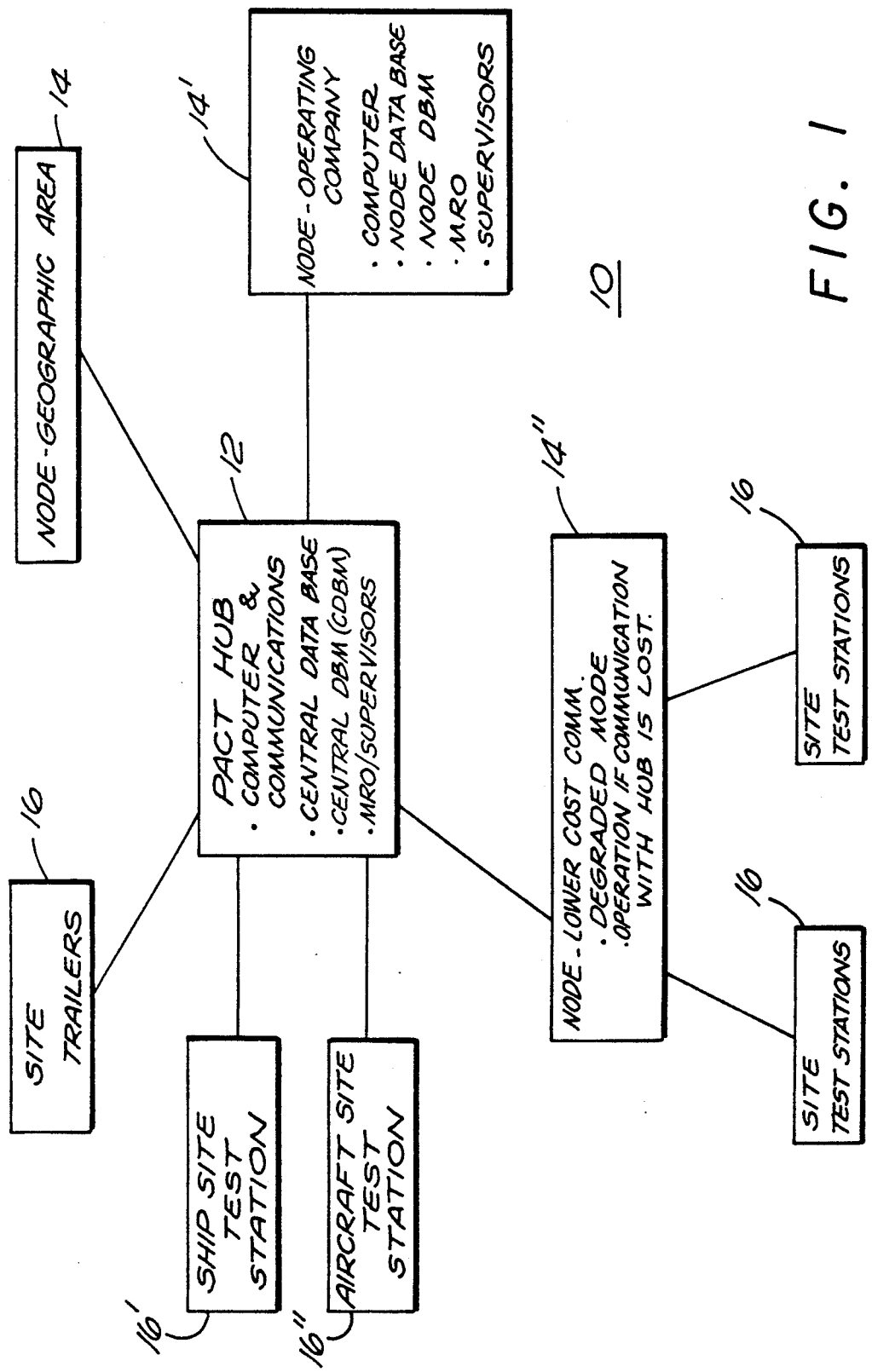
FIG. 1 is a schematic representation of the redundant system for interactively evaluating a subject's current performance level.

FIG. 1 is a schematic representation of the redundant system for interactively evaluating a subject's current performance level. The system 10 is redundant because evaluation and data storage occurs at potentially two levels. Individual test sites 16 contain multiple test stations located at the physical site location of the subjects under evaluation.

These test sites include, but are not limited to trailer test sites 16 parked at the site, or a ship test site 16' or an aircraft test site 16''. Node sites 14 are central data collection facilities which are electronically connected to the multiple test sites 16. Node sites 14 are grouped together based on, for example, geographic considerations and may as in this example receive data from two sites 16 in the same area. The node sites 14' in an alternative embodiment are designated according to the operating company or division of a larger entity like a corporation. Node sites 14 include a computer, node data bases, data base management and performance evaluating personnel capable of maintaining the data of the node data base. If evaluating personnel such as Medical Review Officers (MRO) are not on staff at the test sites 16 then such evaluators at the node site evaluate the personnel subject's current test results compared to their base line. Communications between the individual test sites and the node sites are relatively inexpensive and would be comprised of a modem or microwave transmission.

A second level of review in the system is the system hub 12 which interconnects various node sites as well as individual test sites. The hub 12 comprises a computer and communications capabilities as well as central data base management and additional evaluating personnel. Failure of the system 10 due to a power outage in such a redundant system will not negatively impact the interconnection between the node sites 14 and test sites 16.

Figure 2:
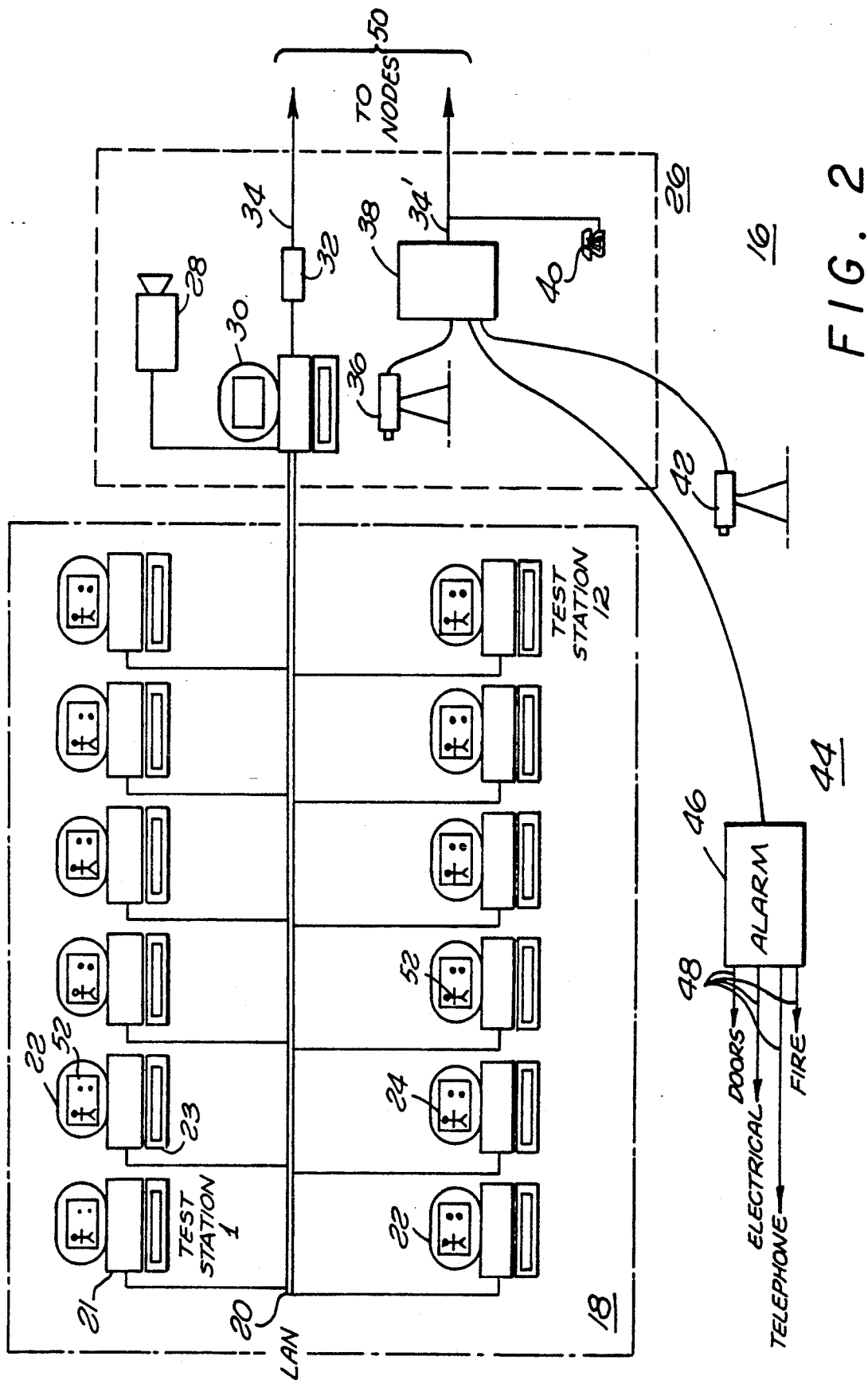
FIG. 2 is a schematic representation of one test site in the system for interactively evaluating a subject's current performance level.

FIG. 2 is a schematic representation of one test site exemplary in the system 10 for interactively evaluating a subject's current performance level. The test site 16 includes at least one test station 21 which is networked into a test station area 18. Each test station contains monitor 22 with view screen 24 and keyboard or any other data input device 23. Subject 17 seated before monitor 22 is presented with tests 52 which appear on the view screen 24. In response to the tests 52, subject 17 depresses keys on the keyboard 23. Performance data generated by subject 17 responses on the keyboard 23 is transmitted over cable 27 and networked through the LAN 20 to a private consultation room 26.

In FIG. 2, twelve test stations 21 are available to simultaneously assess the performance capabilities of twelve subjects 17, however, as many as fifteen test stations are feasible. The subjects 17 log-on the test stations 21 and perform the test. The test results are then compared to their prior stored performance data or base line which may be retrieved from the node sites. Each subject's responses to the test stimuli are sent to node sites through inexpensive communications levels such as modem 32 and telephone line 34 via test station output lines 50.

Security is critical in the evaluation of the subject's 17 performance. The private consultation room 26 contains a video transceiver 38 that incorporates a general surveillance camera 42 trained upon the subjects. In addition, a physical security system 44 with alarm 46 connected to doors, electrical, telephone and fire 48 and a private interview camera 36 are also connected to the transceiver 38. The video transceiver 38 is connected to the node site (not shown here) relaying security sensitive information through telephone line 34'. In the event of a subject's failure of several test 52 sequences an additional test station 30 or a breath analyzer 28 may be used in the private consultation room 26 to secure physical evidence of the subject's 17 condition. This security system 44 is not critical for the interactive test system, but incorporates an alternative approach to employee assessment.

Figure 3:
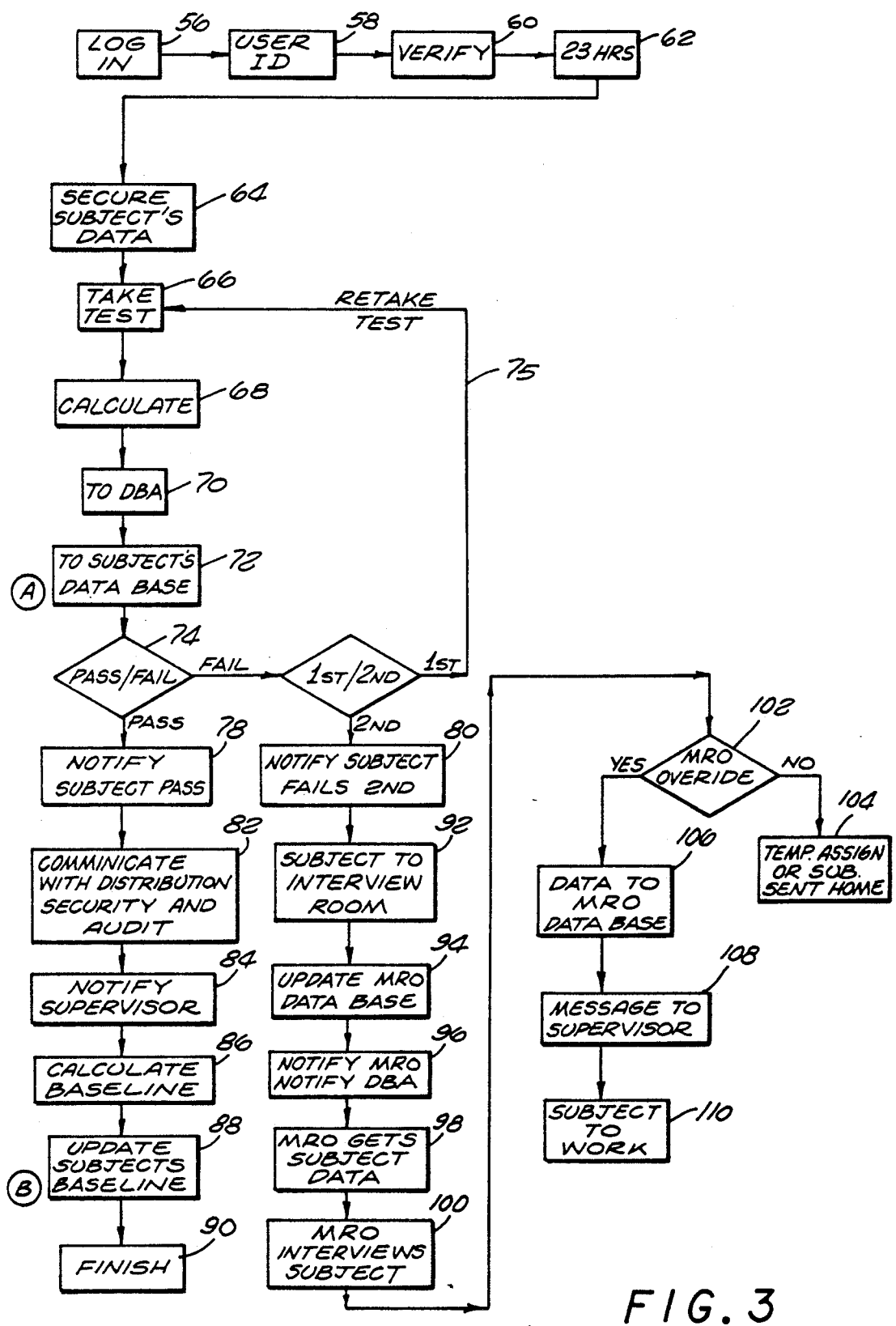
FIG. 3 is a flow chart of the performance evaluation method as implemented by the system.

FIG. 3 is a flow chart of a performance evaluation method 54 as used by the system 10. This method would be best implemented by software programming. The subject 17 (not shown here) first logs in (step 56) and establishes through his user identification number (step 58) his identity that is verified (step 60) by the node site to assure that he exists within the system 10. The system determines if the subject 17 has used the system 54 within the past twenty-three hours (step 62). The node site secures the subject s information data (step 64) stored at the hub or at the node site. The subject 17 (step 66) takes the test 54 and his performance results are calculated (step 68) and transmitted to the data base administration (step 70) where the current test performance results are compared to the subject's 17 historical data base (step 72). If the subject fails, the test is retaken a second time. If the subject 17 passes the test the second time (step 74) he is notified of the pass (step 78) and the passing results are communicated to security and the audit sections of the node site. The subject's supervisor is notified of the passing results (step 84) and the subject's 17 baseline is recalculated, by including the current test results. The subject's baseline is updated (step 88) and the performance evaluation method 54 is complete (step 90).

In FIG. 3 if the subject fails the test (step 66) a second time the subject 17 is notified of the failure (step 80). The subject 17 may be interviewed (step 92) in the private consultation room 26 (not shown here).

As a result of the second failure, the subject's database is updated (step 94) by the node site or hub site medical review officer (MRO). The MRO at the node site or hub, as well as the data base administrator (DBA) are notified of the two failures (step 96). MRO secures the subject's data (step 98) and interviews the subject (step 100). The MRO at the node site or the hub has the option to override the subject's repeated failure of the tests. As shown, (step 102) the MRO can reinstate the subject to their performance task after analysis of the data generated. If the MRO does not override the subject's failure of the tests then the subject is temporarily assigned to a non-safety sensitive job or sent home (step 104). If the MRO does override the test results the failure data is sent to the data base (step 106) and a message is sent to the supervisor (step 108) and the subject is sent to his appointed task step (110).

Figure 4:
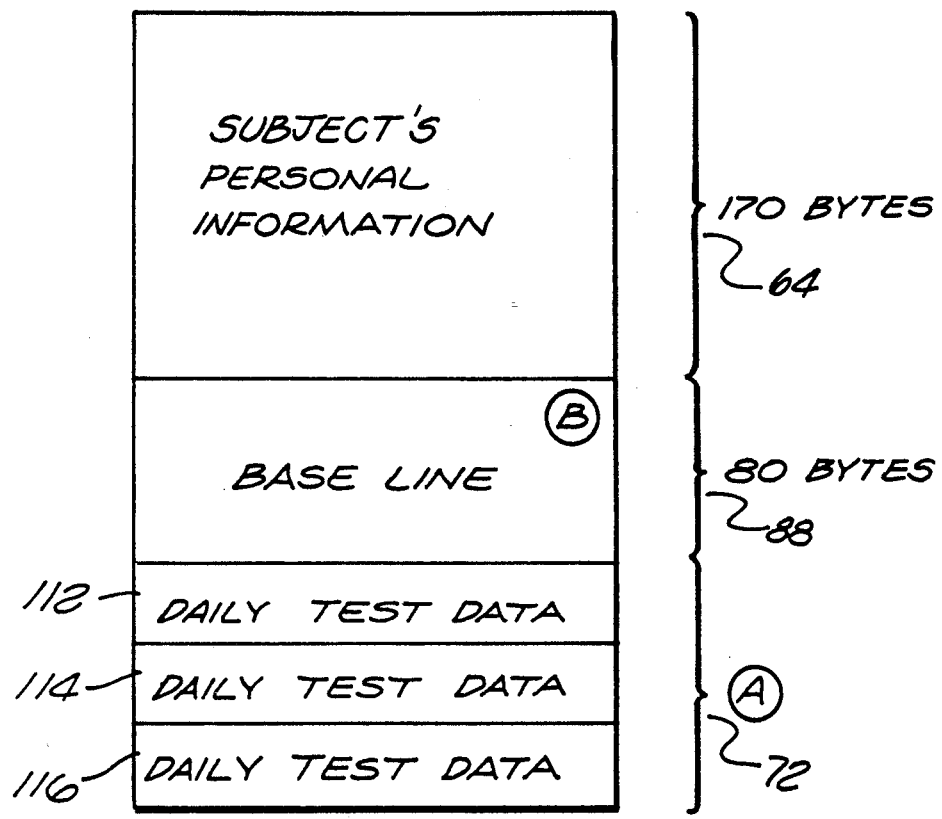
FIG. 4 is a schematic representation of the data base for one subject evaluated by the system.

FIG. 4 is a schematic representation of the data base for one subject evaluated by the system 10. Daily test data 112, 114 and 116 taken over a period of three days produces the subject's original test data base 72. This updated base line 88 is combined with the subject's personal information 64. The subject's test data base line is added to with each days results and such results are accumulated until a predetermined number of test results is included. Thereafter only the immediate past test results for a predetermined number of tests is retained, for example, the last twenty. Therefore, the subject's test data base is continuously updated. The subject's personal information is not maintained at the test site for security reasons and to prevent tampering with the subject's data base.

Figure 5:
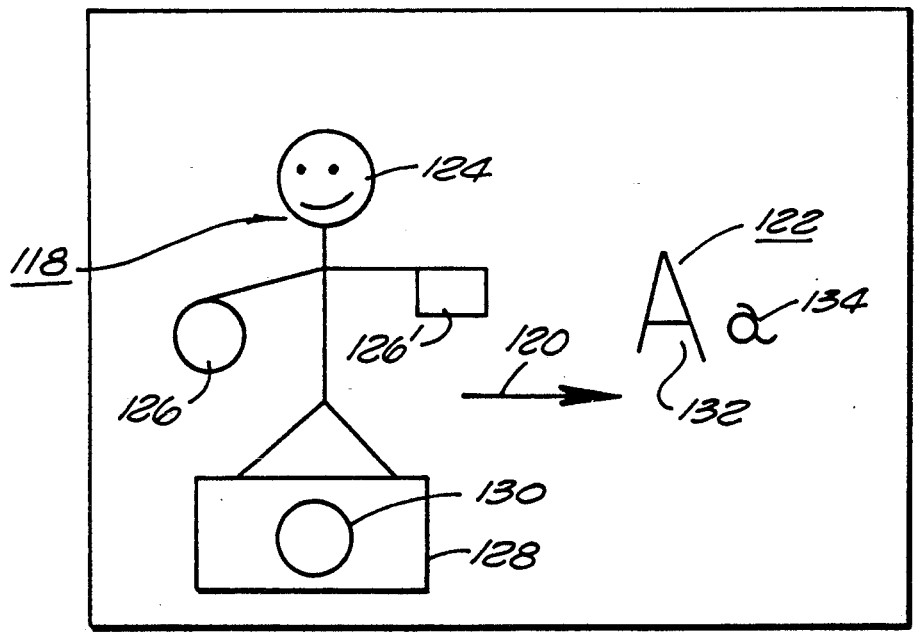
FIG. 5 is a schematic representation of the personal computer monitor screen presenting the spatial and visual attention tests used by the performance evaluation method as presented by the system.

FIG. 5 is a schematic representation of the monitor screen 24 presenting the spatial, visual and attention tests used by the performance evaluation method 54. The test 52 presented to the subject 17 (not shown here) can be the type as described in U.S. patent application Ser. No. 07/465,271 entitled, "Apparatus and Method Determining the Ability of an Individual to Perform a Task". The test 52 described in the application and shown by example in FIG. 5 performs three distinct testing operations. First, a visual test 118 requires the test subject 17 to evaluate a manikin 124 holding objects 126, 126' in a manikin's hands as compared with an object 130 in box 128. An attention test 120 is also incorporated in screen 24. This task is very important because it demonstrates primarily the subject's inability to appreciate whether an arrow 120 is pointing to the visual test 118 or a verbal test 122.

The verbal test 122, shown in FIG. 5 presents two letters 132, 134 to the subject where the subject 17 must assess if letters 132, 134 are the same or different. The keyboard of the interactive computer is so designated to facilitate the subject's response by depressing the preselected keys. The arrow of the attention test 120 randomly switches between the verbal 122 and the visual 118 tests thereby preventing the subject from memorizing sequences of operations and depressing a memorized sequence of keys.

While particular embodiments of the invention have been shown and described, it will be obvious to those skilled in the art that changes and modifications can be made without departing from the invention in its broader aspects and therefore the appended claims are intended to cover all such changes and modifications as followed in the true spirit and scope of the invention.

What is claimed is:

1. A system for interactively evaluating performance capabilities of a plurality of subjects at different and separated locations, comprising:
   a plurality of test sites;
   at least one test station at each of said test sites, said test station having at least one interactive computer means for interfacing with said subject;
   performance evaluation means at said test station for producing current subject performance data representative of said subject's current performance level, said performance evaluation means including means for presenting a verbal and spatial attention test to said subject on said interactive computer means;
   at least one node site;
   means for coupling each of said plurality of test sites, to said at least one node site, said at least one node site operable to communicate with each of said test sites, said at least one node site having a node data base of said subject's past performance data and further operable to store said subject's current performance data from said plurality of test sites and to present both said past and current subject's performance data to evaluating personnel located at said at least one node site;
   a hub site; and
   means for coupling said at least one node site to said hub site, said hub site operable to communicate with said at least one node site and further operable to store said subject's current and past performance data from said at least one node site.

2. A system for interactively evaluating performance capabilities of a plurality of subjects at different and separated locations as defined in claim 1 wherein each of said plurality of test sites includes a plurality of test stations.

3. A system for interactively evaluating performance capabilities of a plurality of subjects at different and separated locations as defined in claim 1 which further includes a plurality of node sites each of said plurality of node sites having a plurality of different test sites coupled thereto, and means coupling each of said node sites to said hub.

4. A system for interactively evaluating performance capabilities of a plurality of subjects at different and separated locations as defined in claim 1 wherein said means for coupling said plurality of test sites to said at least one node site includes modem means and telephone lines.

5. A system for interactively evaluating performance capabilities of a plurality of subjects at different and separated locations as defined in claim 1 wherein at last one of said test sites further includes surveillance means for remotely observing said subject during the time said test is being presented to said subject.

6. A system for interactively evaluating performance capabilities of a plurality of subjects at different and separated locations as defined in claim 5 which further includes means for coupling said surveillance means to said node site.

7. A system for interactively evaluating performance capabilities of a plurality of subjects at different and separated locations as defined in claim 1 wherein at least one of said test sites further includes a consultation area separate from said at least one test station.

8. A system for interactively evaluating performance capabilities of a plurality of subjects at different and separated locations as defined in claim 7 wherein said consultation area further includes camera means for providing a record of said subject's condition when said subject is in said consultation room.

9. A system for interactively evaluating performance capabilities of a plurality of subjects at different and separated locations as defined in claim 8 wherein said consultation room further includes a test station.

10. A system for interactively evaluating performance capabilities of a plurality of subjects at different and separated locations as defined in claim 9 wherein said consultation room further includes a means for testing the breath of said subject.

11. A system for interactively evaluating performance capabilities of a plurality of subjects at different and separated locations as defined in claim 10 wherein said consultation room further includes security alarm means coupled thereto.

12. An interactive method of evaluating performance capabilities of multiple test subjects to perform a task utilizing a computerized test system for comparing each said subject's response to a test to each said subject's previously generated base line, said method comprising the steps of:

(a) verifying the identity of each said test subject after said subject accesses a personal compute, said personal computer having a view screen and keyboard;

(b) determining if each said test subject has been tested within a predetermined period of time;

(c) if step (b) is negative, then accessing said each test subject's previously stored personal performance base line test results from said test subject's data base file, said data base file located physically distant from said personal computer;

(d) testing each said test subject utilizing a predetermined interactive test, said test presented to each said test subject on said personal computer view screen;

(e) recording each said test subject's responses to said test as generated by each said test subject through said personal computer keyboard;

(f) communicating said recorded test results to each said test subject's data base file;

(g) comparing said communicated recorded test results to each said test subject's previously stored personal performance base line test results;

(h) determining if said communicated, recorded test results are different from each said test subject's previously stored test results;

(i) retesting any of said test subjects at least one more time if said communicated, recorded test results are less than that test subject's previously stored base line test results;

(j) conducting an interview said subject if that said subject's retesting test results are less than that said subject's previously stored base line test results; and (k) discharging that said test subject from the performance of said task upon that said test subject's failure to perform satisfactorily during said interview such that said repeated failure of that said subject to produce communicated recorded test results at least equal to said test subject's previously stored base line test results can be overridden.

13. A method as defined in claim 12 wherein said interview is performed by a Medical Review Officer.

14. A method as defined in claim 13 wherein said interview is performed using an interview video camera.

* * * * *